United States Patent [19]
Castaneda

[11] 3,970,087
[45] July 20, 1976

[54] HYGIENIC NAPKIN

[75] Inventor: Rosa Maria Castaneda, Jardin Balbuena, Mexico

[73] Assignee: Colgate-Palmolive Company, New York, N.Y.

[22] Filed: Dec. 30, 1974

[21] Appl. No.: 537,158

[52] U.S. Cl. .............................. 128/290 H
[51] Int. Cl.² ................................. A61F 13/6
[58] Field of Search ............... 128/287–290, 128/286, 290 W, 284

[56] References Cited
UNITED STATES PATENTS

| | | | |
|---|---|---|---|
| 3,460,535 | 8/1969 | Behna | 128/288 |
| 3,643,662 | 2/1972 | McGuire et al. | 128/287 |
| 3,665,922 | 5/1972 | Skora | 128/290 W |
| 3,804,092 | 4/1974 | Tunc | 128/290 W |

Primary Examiner—Lawrence W. Trapp
Attorney, Agent, or Firm—Norman Blumenkopf; Herbert S. Sylvester; Murray M. Grill

[57] ABSTRACT

An hygienic napkin comprising an envelope of liquid penetrable material which is folded and secured in such a manner as to form a pouch for receiving absorbent material therein. The envelope is provided with a flap for closing the pouch and a fluid-impervious sheet is provided for preventing passage of liquids all the way through the envelope.

5 Claims, 5 Drawing Figures

HYGIENIC NAPKIN

BACKGROUND OF THE INVENTION

1. Field of the Invention

This invention relates to a hygienic napkin for feminine use, and more particularly to an envelope for convenient insertion of absorbent material for convenient utilization.

2. Description of the Prior Art

Various types of sanitary napkins and other devices for feminine hygiene have been devised in the past. These sanitary napkins have required the employment of sizable amounts of absorbent material. As a result, because of the cost of the absorbent material and the mass and bulk thereof, packaging of such devices is expensive and the handling and shipment is also expensive. Furthermore, because of the bulk of such devices, drug stores and other retail establishments have had to assign a large area for storage and merchandising for such devices, which is less profitable than higher cost items of small size.

In many locations, women have access to various types of absorbent material such as cotton waste, rags, sawdust, and other cellulosic materials. However, these absorbent materials are generally diffcult to secure in place, and may be loose and in particles of small size. Further, there is little protection provided by the absorbent materials against fluids penetrating the entire mass, and thus staining the clothes or limbs of the user.

SUMMARY OF THE INVENTION

It is therefore the primary object of the present invention to provide a hygienic envelope for receiving therein a desired amount of absorbent materials, and for conveniently mounting the envelope on the garments or body of the user while providing for safeguard against leakage.

The concept of this invention features the use of an envelope formed preferably of a non-woven hydrophobic material but capable in this invention of being made of a woven fabric. The non-woven material or woven fabric can be cotton or polyester fabric as well as any other fibers of animal, vegetable or synthetic origin, either processed for the first time or regenerated. A liner of a thin film of fluid-impervious material made of any suitble plastic material, as for example, polyethylene, polyvinyl, polypropylene, Mylar or non-woven or woven material in any color, or transparent, is provided for preventing the migration of organic or inorganic fluids through the exterior of the envelope so that the liquids that are absorbed in the hygienic envelope do not wet the user's clothing or when used in a hospital, do not stain surgical garments or the bed. Suitable adhesive strips are provided in order to fasten the hygienic envelope to the under-garments or body of the user. The adhesive employed can be of a rubber base, or any combination of natural organic adhesive may be employed and may be of a pressure-sensitive type, as desired.

It is a further object of the invention to provide a do-it-yourself type of sanitary napkin wherein an envelope is sold to the eventual user who can fill the envelope with readily available absorbent material such as rags, cotton waste, paper, sawdust, or other like material.

Still further objects of the invention reside in the provision of an hygienic napkin which can be packaged for sale in a parcel of relatively small size for many envelopes, which is efficient and comfortable to use, and inexpensive to manufacture, thereby permitting wide use and distribution.

These, together with the various ancillary objects and features of the invention which will become apparent as the description proceeds, are attained by this hygienic napkin, a preferred embodiment being shown in the accompanying drawing, by way of example only, wherein:

DETAILED DESCRIPTION OF THE INVENTION

Figure 1:
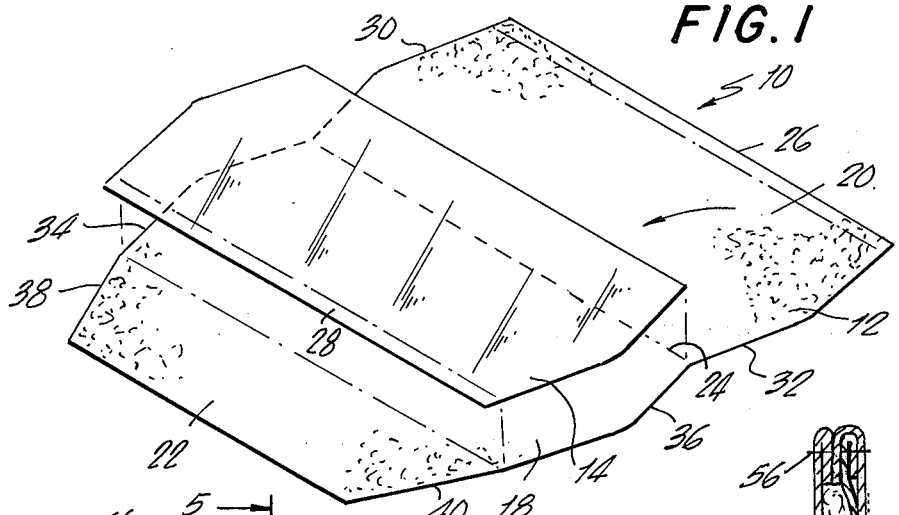
FIG. 1 is an exploded perspective view of the envelope used in a preferred embodiment of the present invention.
Figure 2:
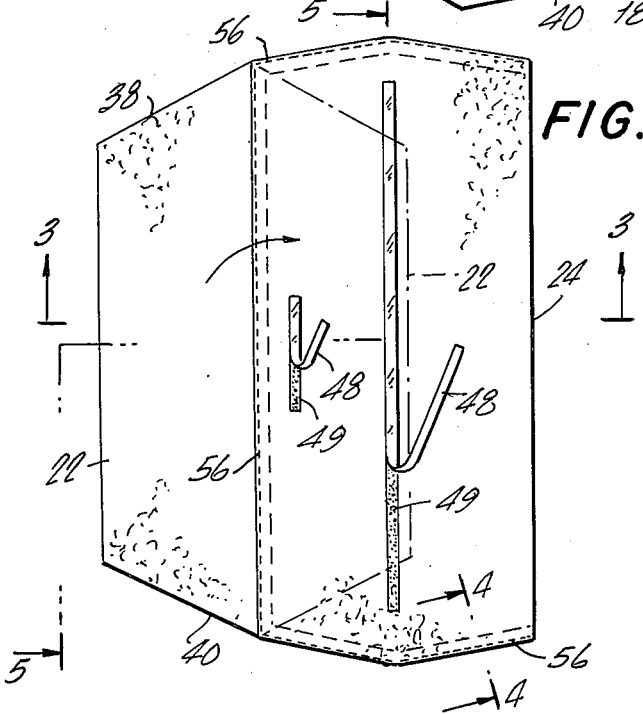
FIG. 2 is a plan view of the hygienic napkin.
Figure 5:
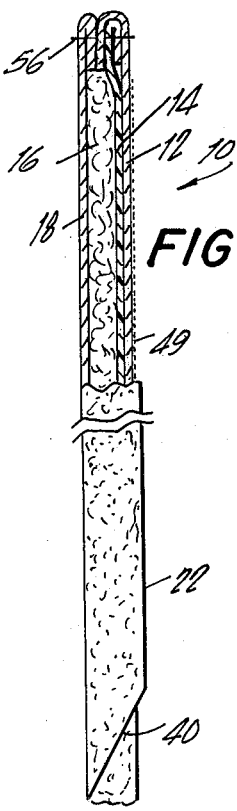
FIG. 5 is an enlarged sectional view taken along the plane of line 5—5 in FIG. 2.
Figure 3:
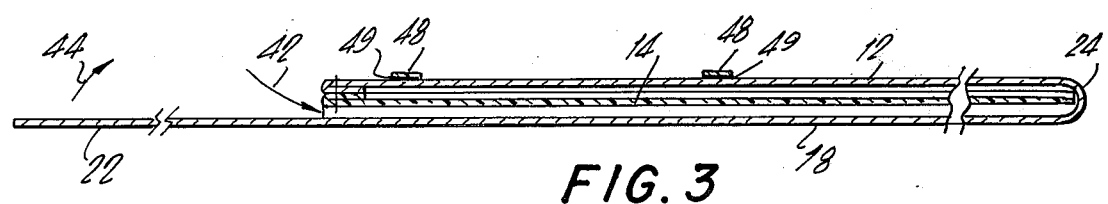
FIG. 3 is an enlarged sectional view taken along the plane of line 3—3 in FIG. 2.

With continuing reference to the accompanying drawing, wherein like reference numerals designate similar parts through the various views, reference numeral 10 generally designates the hygienic napkin constructed in accordance with the concepts of the present invention. This hygienic napkin contains three main parts, an envelope 12, a water-proof sheet 14, and a filling of absorbent material 16.

The envelope 12 is made preferably of a non-woven hydrophobic material. This type of material is such that it permits flow of liquid readily therethrough and through which the moisture does not spread, thereby permitting quick passage of menstrual fluids and the like which is then absorbed by the absorbent material 16, and also provides for a more sanitary condition. Alternatively, the envelope 12 can be a woven fabric as well as being of non-woven material, even though the non-woven hydrophobic material is preferred. The woven material can be fibers of animal, vegetable, or synthetic fibers as desired. The envelope 12 includes a back 20, a front 18, and a flap 22. The back 20 is folded at 24 into overlying position above the sheet 14. The edge 26 of the back 20 is secured to the edge 28 of the sheet as by bonding, heat sealing or welding, or by stitching. Further, the peripheral edges 30 and 32 of the back 20 are secured to the peripheral edges 34 and 36 of the front 18 as by stitching, bonding, heat-sealing or welding. The peripheral edges 30 and 32, and 34 and 36 are tapered to better conform to the contours desired for the particular use, which may also be rounded off as desired. The flap likewise has converging tapered edges 38 and 40.

It is noted that the filling 16, which may be of rags, cotton wastes, paper, sawdust, or any other available cellulosic or non-cellulosic absorbent material, is inserted in the pouch formed between the front 18 and the sheet 14 in the direction of the arrow 42. The sheet 14 is preferably a thin film of polyethylene, but may be made of polyvinyl, polypropylene, Mylar, or non-woven or woven material that is waterproof and may be transparent or of any color. After the absorbent material 16, which may be of a comminuted or small particle size, has been inserted in the pouch in the space between the sheet 14 and the front 18, the flap 22 may be folded in the direction of the arrow 44 to overlie the back.

Coated on the back are adhesive strips as at 49 which are used to hold the flap 22 in a closed position, closing the pouch and retaining the absorbent material 16 in position. The peelable tabs 48 are used to protect the adhesive strips until the sanitary napkin is ready to be inserted within the undergarments of the user. The tabs 48 are removed so that at least a portion of the adhesive strips 49 may be used to fasten the napkin 10 directly to the undergarment of the user. The adhesive strips may be of any rubber base and preferably of pressure-sensitive adhesive or may be formed of any combination of adhesive found to be of non-allergic quality.

Figure 4:
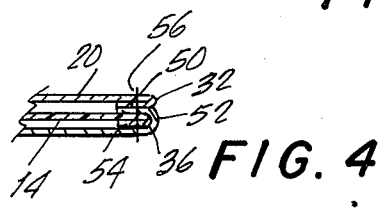
FIG. 4 is an enlarged detail sectional view taken along the plane of line 4—4 in FIG. 3.

As shown in FIG. 4, in the construction of the invention at the peripheral edges, as for example, of the back 20, the peripheral edge 32 is bent over to form a hem 50. Likewise, the front 18 has its peripheral edge at 36 bent over to form a hem 54. Stitching as at 56 or other means of securing the parts together is used to provide for very effective reinforcement and a strong edge, thereby preventing leaking. In use, with the hygienic napkin mounted in position, fluids will pass through the hydrophobic front 18 and will be absorbed by the absorbent material 16. Seepage onto the garments will thereby be prevented.

A latitude of modification, substitution and change is intended in the foregoing disclosure, and in some instances, some features of the invention may be employed without a corresponding use of other features.

What is claimed is:

1. An hygienic napkin comprising an envelope of liquid penetrable non-woven, hydrophobic material or woven fabric, said envelope having opposed longitudinal and lateral edges and including a front portion, a back portion and a flap portion integral with the front portion and foldable to overlie said back portion, a sheet of liquid impervious waterproof material between said front and back portions, means securing said back portion to said front portion along a first opposed lateral edge portion, and wherein said front and back portions are bent inwardly along a second opposed lateral edge portion to form abutting hem portions and means securing said hem portions together.

2. An hygienic napkin according to claim 1, including a filling of absorbent material in said envelope.

3. An hygienic napkin according to claim 1, including adhesive strips coated on said back portion for securing said napkin in position on the user, and removable adhesive tabs overlying said strips for closing said flap portion.

4. An hygienic napkin according to Claim 1, including means securing said sheet to said back portion along said opening.

5. An hygienic napkin according to claim 1, wherein said envelope is of a non-woven hydrophopic material.

* * * * *